United States Patent
Imoto et al.

(10) Patent No.: US 10,261,299 B2
(45) Date of Patent: Apr. 16, 2019

(54) IMAGE-ACQUISITION APPARATUS AND IMAGE-ACQUISITION METHOD

(71) Applicant: OLYMPUS CORPORATION, Tokyo (JP)

(72) Inventors: Kentaro Imoto, Tokyo (JP); Ryusuke Tanaka, Tokyo (JP); Hidenori Tsuboi, Kanagawa (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/102,840

(22) Filed: Aug. 14, 2018

(65) Prior Publication Data

US 2019/0004302 A1  Jan. 3, 2019

Related U.S. Application Data

(63) Continuation of application No. PCT/JP2016/057578, filed on Mar. 10, 2016.

(51) Int. Cl.
*G01N 21/64* (2006.01)
*G02B 21/00* (2006.01)

(52) U.S. Cl.
CPC ......... *G02B 21/0076* (2013.01); *G01N 21/64* (2013.01); *G01N 21/6458* (2013.01);
(Continued)

(58) Field of Classification Search
CPC .............. G02B 21/0076; G02B 21/008; G01N 21/6458; G01N 2021/6463
See application file for complete search history.

(56) References Cited

U.S. PATENT DOCUMENTS 9,506,749 B2 * 11/2016 Bellis ................. G01B 11/2545
9,535,241 B2 * 1/2017 Nomura ................. G02B 21/06
(Continued)

FOREIGN PATENT DOCUMENTS

EP   1835323 A1   9/2007
EP   2063306 A1   5/2009
(Continued)

OTHER PUBLICATIONS

International Search Report dated Jun. 7, 2016 issued in PCT/JP2016/057578.

*Primary Examiner* — David P Porta
*Assistant Examiner* — Djura Malevic
(74) *Attorney, Agent, or Firm* — Scully, Scott, Murphy & Presser, P.C.

(57) ABSTRACT

Provided is an image-acquisition apparatus including: a scanning portion that scans illumination light emitted from a light source; an optical system that focuses the scanned illumination light on a sample, while collecting signal light beams generated at the individual scanning positions on the sample; a detector that detects the collected signal light beams and that generates detection signals thereof; a signal controller that is configured to generate periodic signals that are repeated at a predetermined period; a light controller that is configured to temporally control a position or an intensity of the illumination light in accordance with the generated periodic signals; and a computer that is configured to process, in accordance with the generated periodic signals, the detection signals generated, wherein the computer is provided with a frequency shifter for shifting frequencies of the detection signals, and an integrator that integrates the shifted detection signals at an integration time.

8 Claims, 8 Drawing Sheets

(52) U.S. Cl.
CPC .......... *G02B 21/00* (2013.01); *G02B 21/008* (2013.01); *G01N 2021/6463* (2013.01)

(56) References Cited

U.S. PATENT DOCUMENTS

| | | | |
|---|---|---|---|
| 2005/0117172 A1* | 6/2005 | Plannann | G02B 21/06 356/604 |
| 2008/0215272 A1 | 9/2008 | Fujita et al. | |
| 2009/0135476 A1 | 5/2009 | Araya | |
| 2010/0166293 A1* | 7/2010 | Sugita | A61B 3/102 382/154 |
| 2011/0226965 A1* | 9/2011 | Wolleschensky | G01N 21/6458 250/459.1 |
| 2011/0292405 A1* | 12/2011 | Dunn | G01B 9/02004 356/511 |
| 2012/0038907 A1 | 2/2012 | Schreiber | |
| 2012/0081535 A1* | 4/2012 | Hayashi | G02B 21/0032 348/79 |
| 2014/0043606 A1 | 2/2014 | Ozeki et al. | |
| 2014/0168011 A1 | 6/2014 | Houchi | |
| 2015/0249496 A1* | 9/2015 | Muijs | H04B 10/116 398/118 |
| 2016/0109546 A1* | 4/2016 | Machii | G01R 33/56554 324/322 |
| 2017/0010453 A1 | 1/2017 | Imoto et al. | |

FOREIGN PATENT DOCUMENTS

| | | |
|---|---|---|
| JP | 2009-152545 A | 7/2009 |
| JP | 2011-199939 A | 10/2011 |
| JP | 2012-042467 | 3/2012 |
| JP | 2014-507627 A | 3/2014 |
| JP | 2014-120862 A | 6/2014 |
| WO | WO 2006/061947 A1 | 6/2006 |
| WO | WO 2014/027449 A1 | 2/2014 |
| WO | WO 2015/030202 A1 | 3/2015 |
| WO | WO 2015/163261 A1 | 10/2015 |
| WO | WO 2017/022096 A1 | 2/2017 |

\* cited by examiner

IMAGE-ACQUISITION APPARATUS AND IMAGE-ACQUISITION METHOD

CROSS-REFERENCE TO RELATED APPLICATIONS

This is a continuation of International Application PCT/JP2016/057578, with an international filing date of Mar. 10, 2016, which is hereby incorporated by reference herein in its entirety.

TECHNICAL FIELD

The present invention relates to an image-acquisition apparatus and an image-acquisition method.

BACKGROUND ART

There are known image-acquisition methods in which a lock-in amplifier is used in order to form an image by detecting minute signals mixed in strong signals (for example, see Patent Literatures 1 to 4).

CITATION LIST

Patent Literature

{PTL 1} WO2006/061947
{PTL 2} WO2015/030202
{PTL 3} Japanese Translation of PCT International Application, Publication No. 2014-507627
{PTL 4} WO2014/027449

SUMMARY OF INVENTION

An aspect of the present invention is an image-acquisition apparatus including: a scanning portion that scans illumination light emitted from a light source; an optical system that focuses the illumination light scanned by the scanning portion on a sample, while collecting signal light beams generated at the individual scanning positions on the sample; a detector that detects the signal light beams collected by the optical system and that generates detection signals thereof; a signal controller that is configured to generate periodic signals that are repeated at a predetermined period; a light controller that is configured to temporally control a position or an intensity of the illumination light in accordance with the periodic signals generated by the signal controller; and a computer that is configured to process, in accordance with the periodic signals generated by the signal controller, the detection signals generated by the detector, wherein the computer is provided with a frequency shifter for shifting frequencies of the detection signals by an amount corresponding to the period of the periodic signal generated by the signal controller, and an integrator that integrates the detection signals, which have been shifted by the frequency shifter, at an integration time that is an integer multiple of the period of the periodic signals.

Another aspect of the present invention is an image-acquisition method including: a modulating step of temporally controlling, in accordance with periodic signals that are repeated at a predetermined period, a position or an intensity of illumination light emitted from a light source; a scanning step of scanning the illumination light controlled in the modulating step on a sample; a detecting step of detecting signal light beams generated at the individual scanning positions scanned in the scanning step and generating detection signals thereof; a frequency shifting step of shifting frequencies of the detection signals generated in the detecting step by an amount corresponding to the period of the periodic signals; and an integrating step of integrating the detection signals, which have been shifted in the frequency shifting step, at an integration time that is an integer multiple of the period of the periodic signals.

DESCRIPTION OF EMBODIMENT

Figure 1:
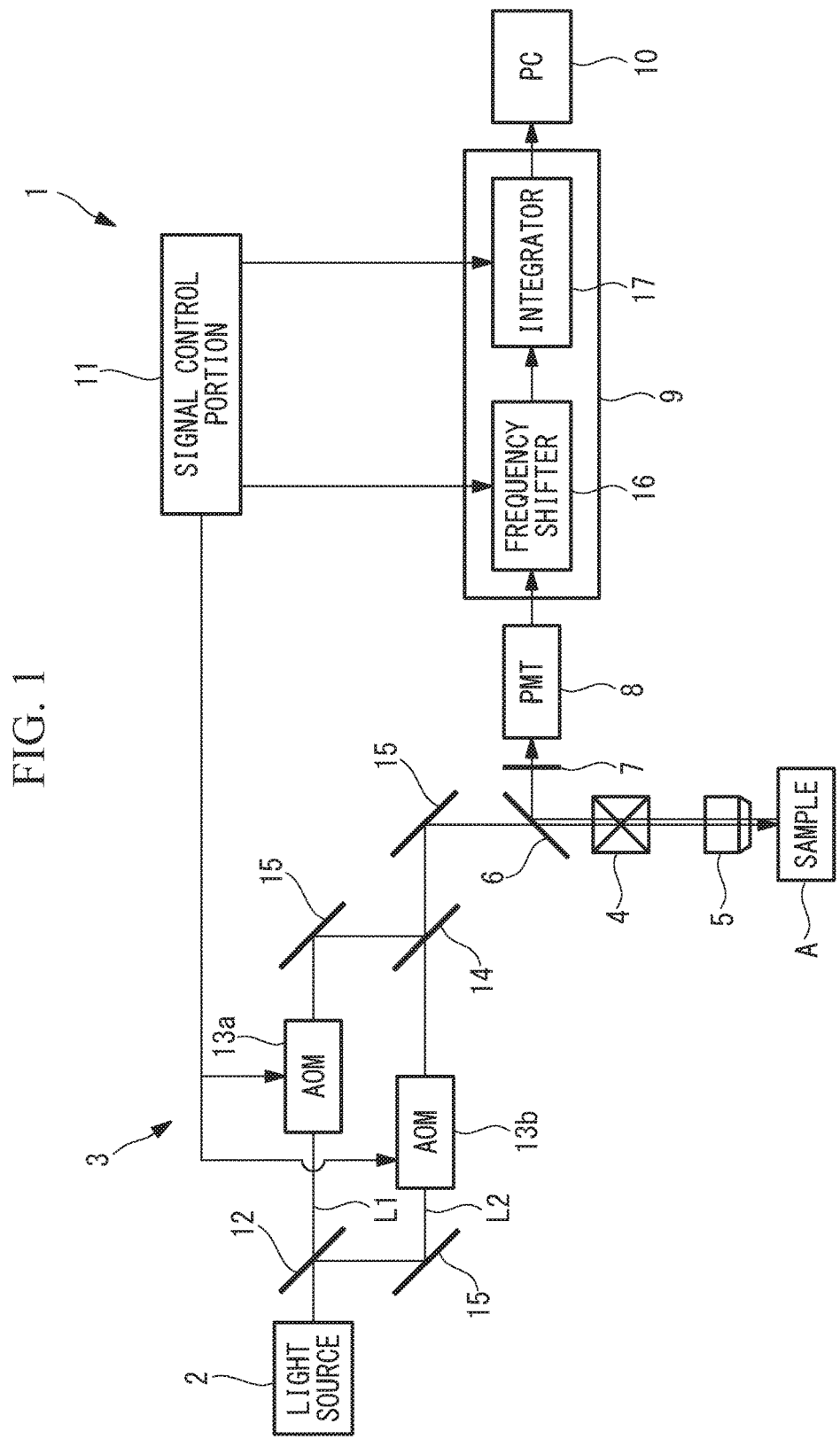
FIG. 1 is a block diagram showing an image-acquisition apparatus according to an embodiment of the present invention.

An image-acquisition apparatus 1 according to an embodiment of the present invention will be described below with reference to the drawings.

The image-acquisition apparatus 1 according to this embodiment is a confocal microscope provided with: a light source 2 that emits a laser beam (illumination light); and a light control portion (light controller) 3 temporally modulates the position of the laser beam coming from the light source 2. In addition, the image-acquisition apparatus 1 is provided with: a scanner (scanning portion) 4 that two-dimensionally scans the laser beam that has been temporally modulated by the light control portion 3; and an objective lens (optical system) 5. The objective lens 5 focuses the laser beam scanned by the scanner 4 onto a sample A, while collecting fluorescence generated at positions in the sample A irradiated with the laser beam.

In addition, the image-acquisition apparatus 1 is provided with: a dichroic mirror 6, a pinhole 7, and a detector (PMT: photomultiplier tube) 8. The dichroic mirror 6 separates the fluorescence collected by the objective lens 5 and returning via the scanner 4 from the optical path of the laser beam. The pinhole 7 is disposed at a position that is optically conjugate with the focal position of the objective lens 5. The detector 8 generates detection signals by detecting the fluorescence that has passed through the pinhole 7.

Furthermore, the image-acquisition apparatus 1 is provided with: a computing portion (computer) 9 that processes the detection signals generated by the detector 8; and an image-processing portion (PC: personal computer) 10 that generates an image on the basis of the detection signals processed by the computing portion 9.

In addition, the light control portion 3 and the computing portion 9 are connected to a signal control portion (signal controller) 11 that generates signals of a predetermined period for synchronizing these components.

In this embodiment, the light control portion 3 is provided with: a first beam splitter 12; acousto-optic modulators (AOM) 13a and 13b; and a second beam splitter 14. The first beam splitter 12 splits the laser beam coming from the light source 2 into two optical paths L1 and L2. The acousto-optic modulators 13a and 13b are individually provided in the optical paths L1 and L2 split by the first beam splitter 12. The second beam splitter 14 combines the laser beams modulated by the individual acousto-optic modulators 13a and 13b. In the figure, reference sign 15 indicates mirrors that form the optical paths.

One optical path L1 is set so that, by displacing the optical axis by means of the mirrors 15, the two laser beams that have been combined by the second beam splitter 14 are made incident on the scanner 4 at different angles. By doing so, the laser beam that has passed through the one optical path L1 is focused at a position on the sample A that is optically non-conjugate with the pinhole 7. The laser beam that has passed through the other optical path L2 is focused at a position on the sample A that is optically conjugate with the pinhole 7.

The two acousto-optic modulators 13a and 13b are configured so as to be operated exclusively of each other in accordance with the periodic signals output from the signal control portion 11. In other words, by operating the two acousto-optic modulators 13a and 13b in synchronization with the periodic signals, the laser beam intensity emitted from the light source 2 is increased and decreased in a temporally alternating manner at the timing at which the intensities of the laser beams passing through the two optical paths L1 and L2 are inverted. As shown in FIG. 2(a), the laser beam emitted from the light source 2 is generated, in an alternating manner, in the form of the laser beam focused at the conjugate position and the laser beam focused at the non-conjugate position, so that the laser beam is temporally switched between two states in which the positions thereof are different.

As shown in FIG. 1, the computing portion 9 is provided with: a frequency shifter 16; an integrator 17; and an A/D converter (not shown).

The detection signals detected by the detector 8 are converted to digital signals by the A/D converter and are subsequently input to the frequency shifter 16.

The frequency shifter 16 shifts the frequencies of the detection signals generated by the detector 8 by an amount corresponding to the period of the periodic signals generated by the signal control portion 11. In this embodiment, the frequency shifter 16 is a digital frequency shifter for assigning signs to the signals at a timing synchronized with the periodic signals. On the other hand, in another embodiment, the frequency shifter 16 may use a method in which positive or negative signs are assigned by means of a switch in an electric circuit, and there is no limitation to the described means and method.

For example, as a result of irradiating the sample A with the laser beams in FIG. 2(a), the generated fluorescence is detected by the detector 8, and thus, the detection signals thereof are generated. When the generated detection signals pass through the frequency shifter 16 in the situation shown in FIG. 2(b), the sign of the fluorescence generated at the non-conjugate position is inverted, as shown in FIG. 2(c).

Figure 2:
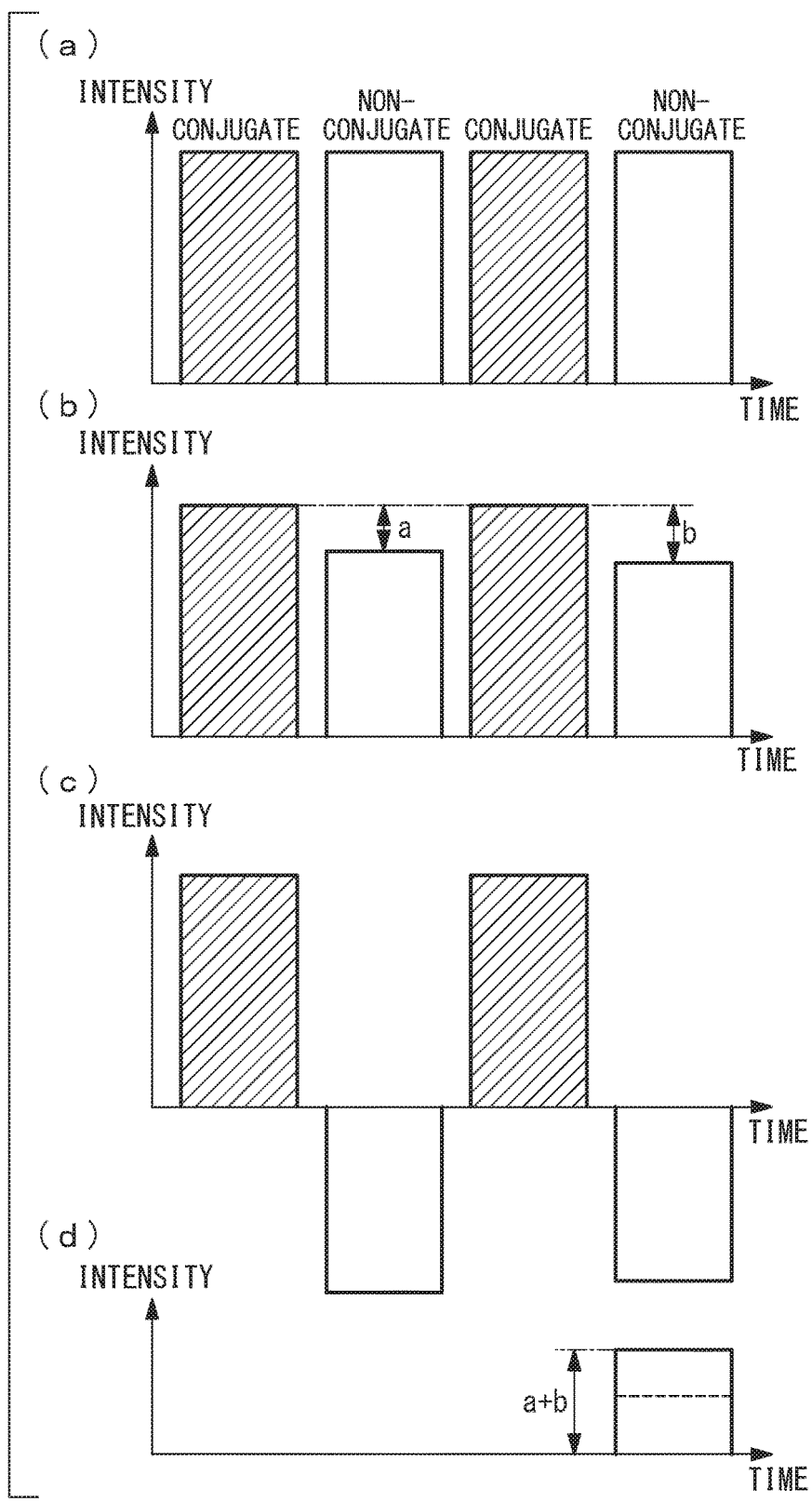
FIG. 2 is a diagram showing, for the image-acquisition apparatus in FIG. 1, (a) laser beams output from a light control portion, (b) fluorescence detection signals detected by a detector, (c) detection signals after being shifted by a frequency shifter, and (d) a detection signal after being integrated.
Figure 3:
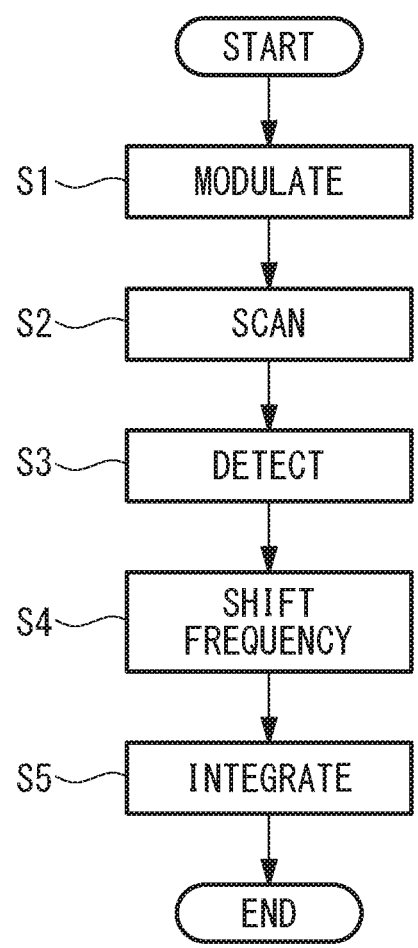
FIG. 3 is a flow diagram showing an image-acquisition method according to an embodiment of the present invention.

The integrator 17 integrates outputs from the frequency shifter 16 at an integration time that is an integer multiple of the period of the periodic signals generated by the signal control portion 11. In the example shown in FIG. 2, integration is performed at an integration time that is twice the period of the periodic signals. FIG. 2(d) shows an output from the integrator 17.

By doing so, it is possible to calculate fluorescence in which out-of-focus fluorescence is subtracted from fluorescence containing, in a mixed state, fluorescence generated at the focal position of the objective lens 5 and the out-of-focus fluorescence generated in an out-of-focus state, in other words, only the fluorescence generated at the focal position of the objective lens 5.

The image-processing portion 10 generates fluorescence images of the sample A by associating the fluorescence intensities output from the computing portion 9 with information about the positions scanned by the scanner 4 at the times at which the fluorescence was detected. Because the fluorescence intensities output from the computing portion 9 do not include out-of-focus fluorescence intensities, the image-processing portion 10 can acquire low-noise, clear fluorescence images.

An image-acquisition method employing the thus-configured image-acquisition apparatus 1 according to this embodiment will be described below.

The image-acquisition method according to this embodiment includes: a modulating step S1, a scanning step S2, a detecting step S3, a frequency shifting step S4, and an integrating step S5. In the modulating step S1, the signal control portion 11 temporally modulates, in accordance with the generated periodic signals that are repeated at the predetermined period, the position of the laser beam emitted from the light source 2. In the scanning step S2, the scanner 4 scans the modulated laser beam on the sample A. In the detecting step S3, the detector 8 generates the detection signals by detecting the fluorescence generated at the individual scanning positions of the scanned laser beam. In the frequency shifting step S4, the signal control portion 11 shifts the frequencies of the generated detection signals by an amount corresponding to the period of the generated periodic signals. In the integrating step S5, the signal control portion 11 integrates the shifted detection signals at an integration time that is an integer multiple of the period of the generated periodic signals.

As has been described above, with the image-acquisition apparatus 1 according to this embodiment and the image-acquisition method therefor, the computing portion 9 demodulates the fluorescence generated at the focal position of the objective lens 5 by means of the frequency shifter 16 and the integrator 17. By doing so, a refresh rate required when using a lock-in amplifier is not needed, and thus, there is an advantage in that it is possible to acquire a fluorescence image having the required sensitivity with a short exposure time. In contrast, by using a lock-in amplifier to achieve exposure at an exposure time for obtaining a fluorescence image having the required sensitivity, there is an advantage in that it is possible to acquire a sufficiently bright fluorescence image.

Note that, although this embodiment has been described in terms of a case in which a fluorescence image in which out-of-focus fluorescence is removed in the image-acquisition apparatus 1 formed of a confocal microscope, there is no limitation to the form of the above-described embodiment.

The signal control portion 11 may have a phase adjusting function for adjusting, with reference to the periodic signal to be input to one of the light control portion 3, the frequency shifter 16, and the integrator 17, the phases of the periodic signals to be input to the other two components so that the other two components are operated together.

In addition, although the signal control portion 11 is provided as a separate apparatus from the light control portion 3, the frequency shifter 16, and the integrator 17, alternatively, the signal control portion 11 may be provided in one of the light control portion 3, the frequency shifter 16, and the integrator 17.

For example, the signal control portion 11 may be provided in the light control portion 3, the light control portion 3 may be controlled by using periodic signals generated by the light control portion 3 itself, and the frequency shifter 16 and the integrator 17 may be controlled by the periodic signals generated by the light control portion 3.

In addition, in this embodiment, a digital frequency shifter is employed as the frequency shifter 16 of the computing portion 9, and a digital integrator is employed as the integrator 17. Because the signs are assigned by means of software after performing A/D conversion, there is an advantage in that it is possible to perform frequency shifting without changing hardware even if the signal waveform changes.

Alternatively, a multiplier formed of an analog circuit may be employed as the frequency shifter 16, and an integrator formed of an analog circuit may be employed as the integrator 17. In addition, a multiplier formed of an analog circuit may be employed as the frequency shifter 16, and a digital integrator may be employed in addition to providing an A/D converter that converts outputs from the multiplier to digital signals.

By employing a multiplier formed of an analog circuit as the frequency shifter 16, there is an advantage in that it is possible to accurately perform frequency shifting, and it is possible to prevent the detection signals from being missed when performing integration.

In addition, by employing a digital integrator as the integrator 17, time for releasing capacitor charge is not required, and thus, there is an advantage in that it is possible to perform high-speed processing.

In addition, it is preferable that an offset adjusting function be provided in the A/D converter that converts the detection signals detected by the detector 8 to digital signals.

This affords an advantage in that it is possible to cancel out noise by performing offset adjustment, and that it is possible to allocate greater amounts of memory to desired signals, thus making it possible to enhance the dynamic range.

In addition, although a case in which the acousto-optic modulators 13a and 13b are employed so as to serve as the light control portion 3 has been described, alternatively, for example, a combination of an acousto-optic device, an electro-optical device, an ND filter, a waveplate, and a polarizer which modulate the laser beam intensity may be employed. In addition, the laser light source itself may be controlled directly.

In addition, as the light control portion 3, an acousto-optic deflector, an electro-optic deflector, or the like that changes the direction in which the laser beam travels may be employed.

Figure 4:
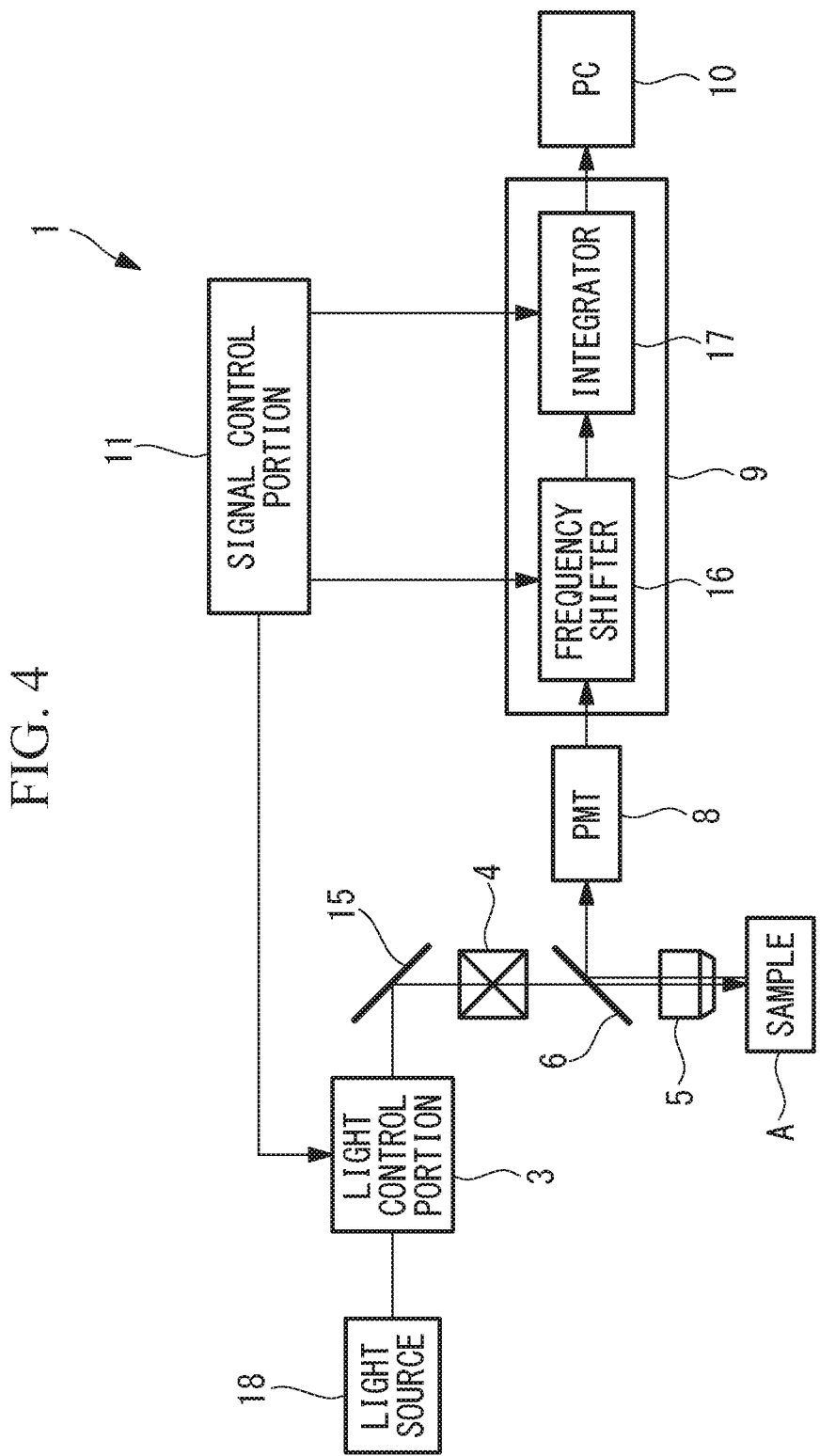
FIG. 4 is a block diagram showing a first modification of the image-acquisition apparatus in FIG. 1.
Figure 5:
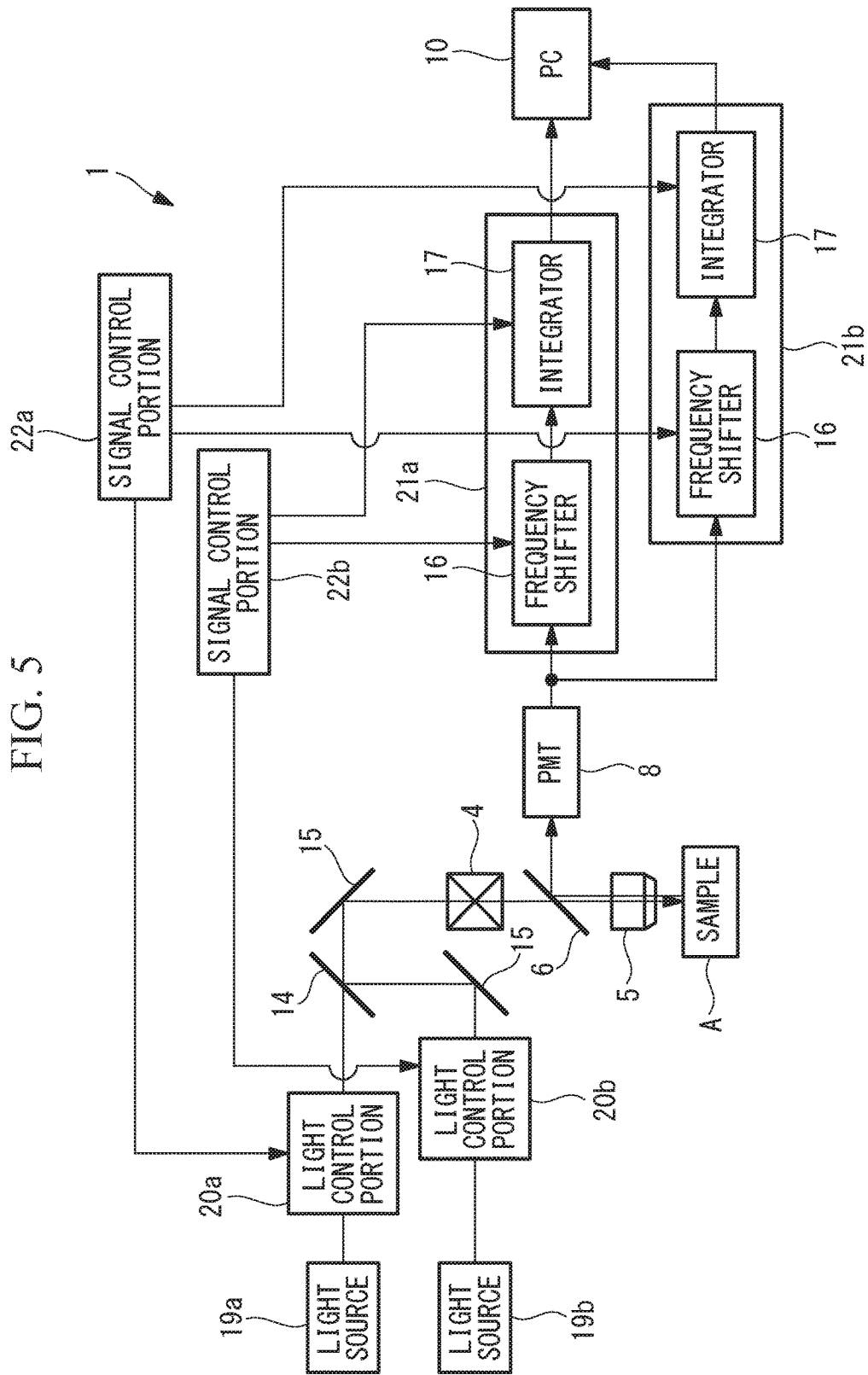
FIG. 5 is a block diagram showing a second modification of the image-acquisition apparatus in FIG. 1.
Figure 6:
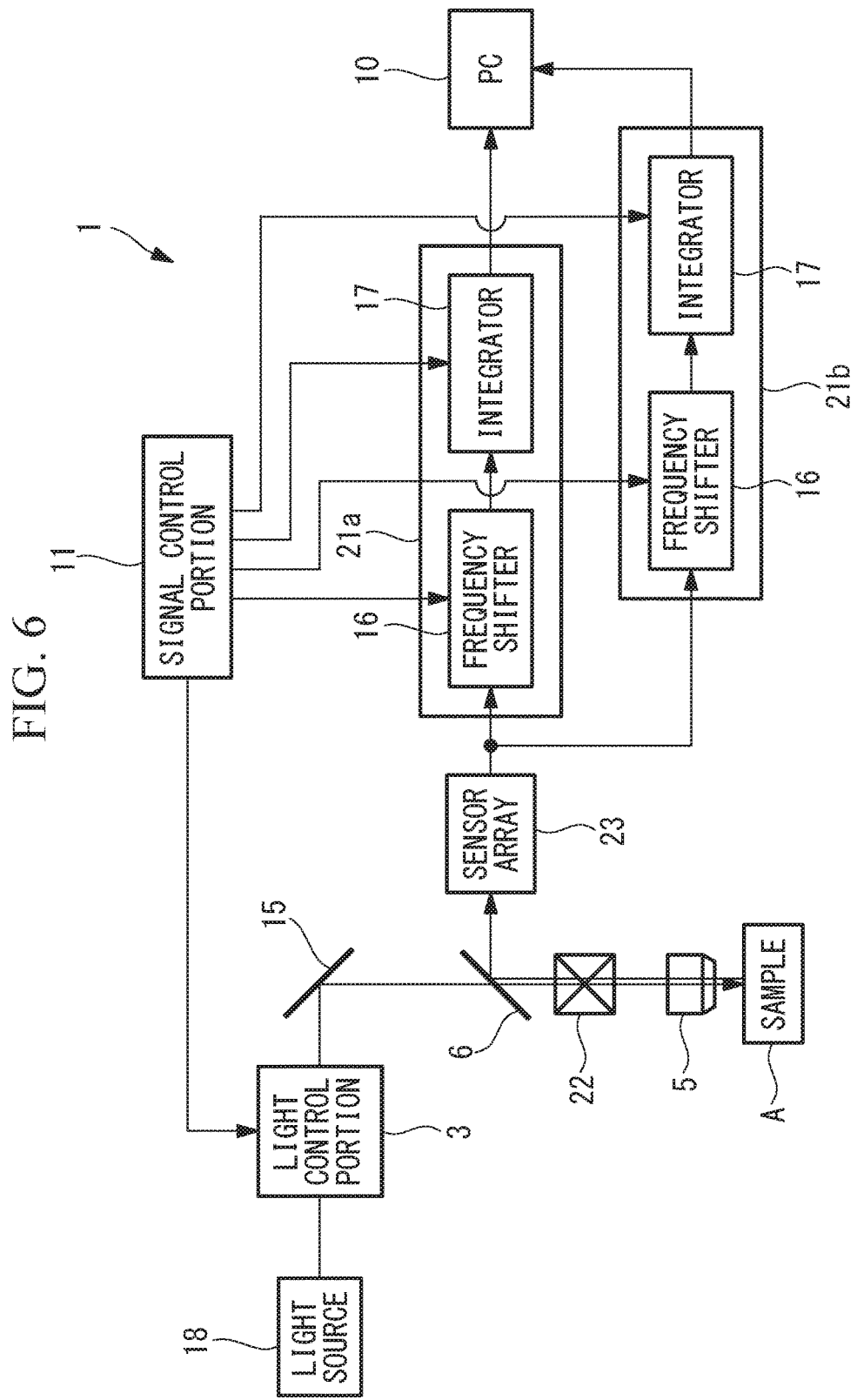
FIG. 6 is a block diagram showing a third modification of the image-acquisition apparatus in FIG. 1.
Figure 7:
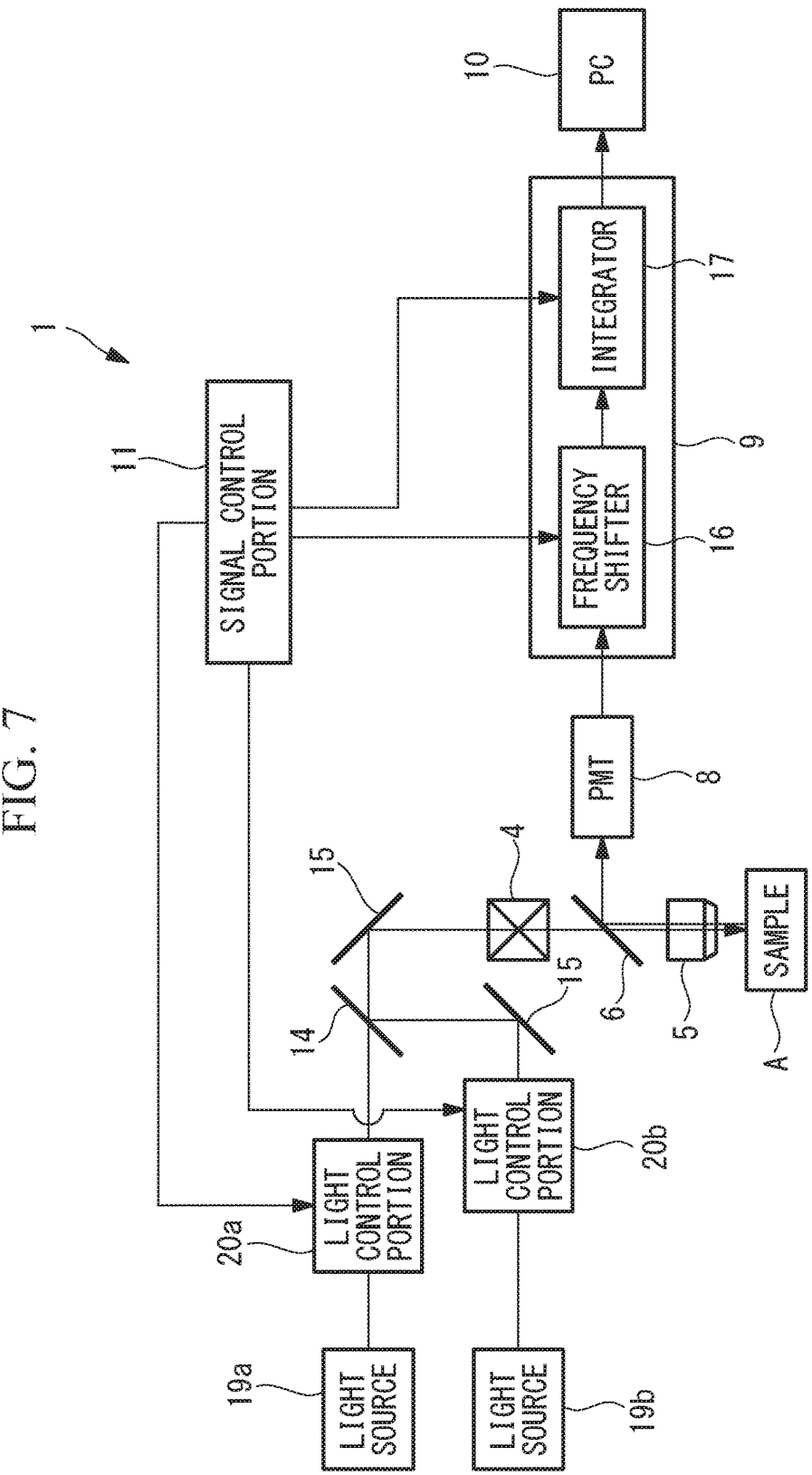
FIG. 7 is a block diagram showing a fourth modification of the image-acquisition apparatus in FIG. 1.

In addition, instead of a confocal microscope, as shown in FIGS. 4 to 6, a multiphoton excitation microscope may be employed or, as shown in FIG. 7, a nonlinear microscope may be employed.

In the example shown in FIG. 4, a light source 18 is a laser light source that emits an ultrashort pulsed laser beam, and the dichroic mirror 6, which splits the fluorescence off from the optical path of the ultrashort pulsed laser beam, is disposed between the objective lens 5 and the scanner 4. In addition, the pinhole 7 shown in FIG. 1 is omitted.

In addition, the example shown in FIG. 5 is provided with: two laser light sources (light sources) 19a and 19b; two light control portions 20a and 20b; two computing portions 21a and 21b; and two signal control portions 22a and 22b. The laser light sources (light sources) 19a and 19b emit ultrashort pulsed laser beams having different wavelengths. The light control portions 20a and 20b individually modulate the ultrashort pulsed laser beams coming from the individual laser light sources 19a and 19b by using different patterns. The computing portions 21a and 21b demodulate desired fluorescences from the detected fluorescences. The signal control portions 22a and 22b supply different periodic signals to the two sets of light control portions 20a and 20b and the computing portions 21a and 21b. By doing so, it is possible to simultaneously acquire two fluorescence signals. In addition, there is an advantage in that it is possible to perform spectroscopy without providing a spectroscopy device. Although the signal control portions 22a and 22b, light control portions 20a and 20b, and computing portions 21a and 21b are provided in two sets, alternatively, three or more sets may be provided.

In addition, as shown in FIG. 6, only the computing portions 21a and 21b may be provided as a set of two, and a single light control portion 3 and the set of two computing portions 21a and 21b may be operated in a synchronized manner in accordance to the periodic signals from the single signal control portion 11. In this example, a multispot scanner, such as a Nipkow disk, is employed as the scanner 22, and a sensor array is employed as the detector 23. The two computing portions 21a and 21b are provided so as to correspond to the laser beams traveling via a plurality of optical paths split by the Nipkow disk. The optical modulation controls the light source intensities, the focused fluorescence is switched between the saturated and non-saturated states, an image is formed on the basis of the difference between the saturated and non-saturated states, and thus, it is possible to enhance the resolution.

In addition, as shown in FIG. 7, the light sources 19a and 19b and light control portions 20a and 20b may be provided in two sets, and the light control portions 20a and 20b and the single computing portion 9 may be operated in a synchronized manner in accordance with the periodic signals from the single signal control portion 11. By employing such a configuration, it is possible to apply the present invention to a nonlinear microscope such as an SRS (stimulated Raman scattering) microscope which is operated by utilizing molecular vibrations of the sample A that are generated by a frequency difference when irradiating the sample A with two types of laser beams having different frequencies in a superimposed manner. The two light sources 19a and 19b are laser light sources that emit ultrashort pulsed laser beams having different wavelengths, and the periodic signals transmitted to the computing portion 9 are synchronized with, for example, the periodic signals transmitted to the light control portion 20a with which one of the ultrashort pulsed laser beams is modulated.

Figure 8:
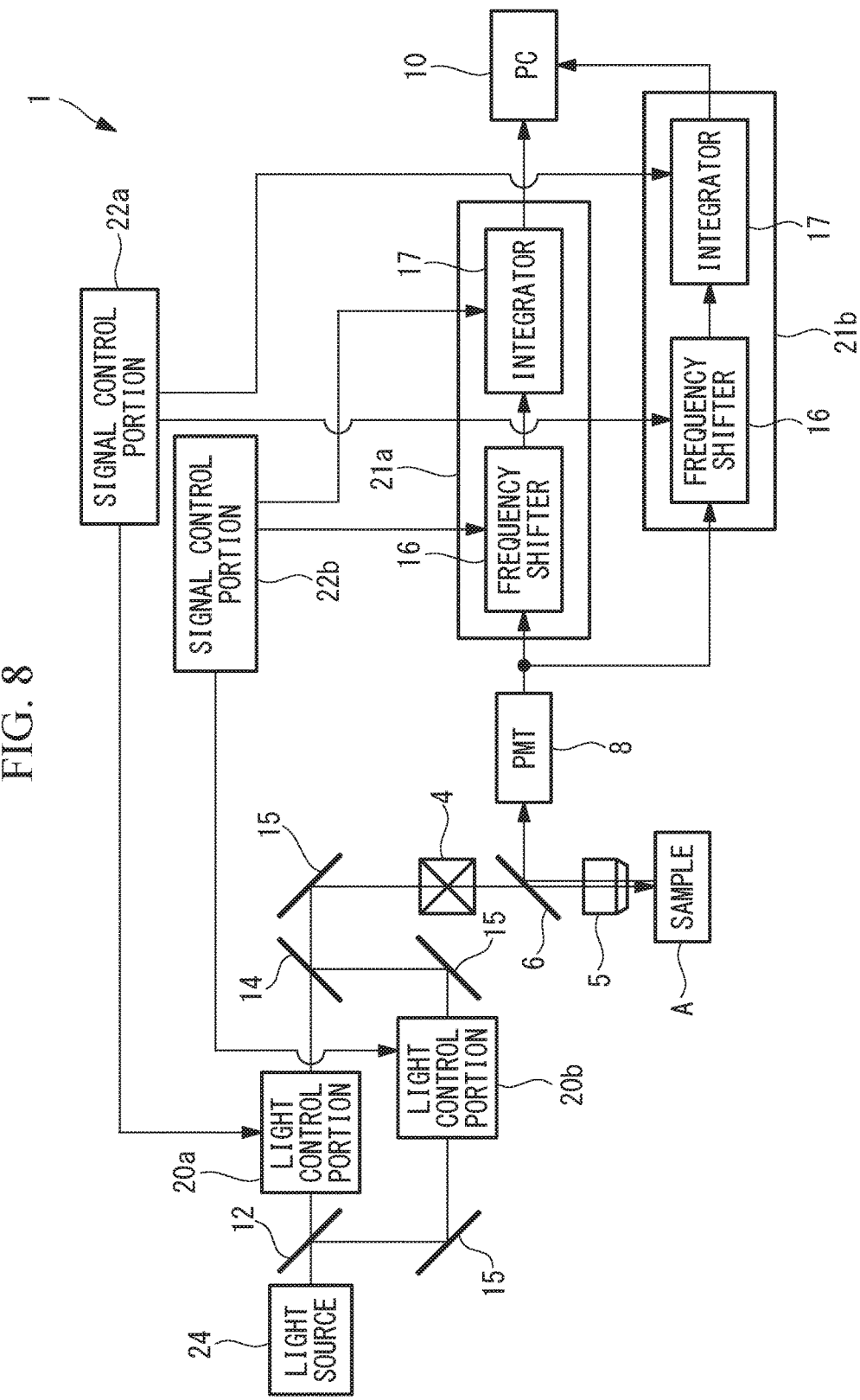
FIG. 8 is a block diagram showing a fifth modification of the image-acquisition apparatus in FIG. 1.

In addition, as shown in FIG. 8, instead of the two laser light sources 19a and 19b in FIG. 5, a single laser light source 24 that emits an ultrashort pulsed laser beam may be employed, and the light control portions 20a and 20b may individually be disposed in the two optical paths L1 and L2 split by the beam splitter 12. The two laser light sources 19a and 19b that emit ultrashort pulsed laser beams having the same wavelength may be employed without using the beam splitter 12. By modulating ultrashort pulsed laser beams that are focused at different positions at different repetition periods and by demodulating the ultrashort pulsed laser beams by means of the two computing portions 21a and 21b, it is possible to simultaneously acquire signals at two points, and thus, it is possible to enhance the image-acquisition speed.

Consequently, the following aspects are derived from the above-described embodiment.

An aspect of the present invention is an image-acquisition apparatus including: a scanning portion that scans illumination light emitted from a light source; an optical system that focuses the illumination light scanned by the scanning portion on a sample, while collecting signal light beams generated at the individual scanning positions on the sample; a detector that detects the signal light beams collected by the optical system and that generates detection signals thereof; a signal controller that is configured to generate periodic signals that are repeated at a predetermined period; a light controller that is configured to temporally control a position or an intensity of the illumination light in accordance with the periodic signals generated by the signal controller; and a computer that is configured to process, in accordance with the periodic signals generated by the signal controller, the detection signals generated by the detector, wherein the computer is provided with a frequency shifter for shifting frequencies of the detection signals by an amount corresponding to the period of the periodic signals generated by the signal controller, and an integrator that integrates the detection signals, which have been shifted by the frequency shifter, at an integration time that is an integer multiple of the period of the periodic signals.

With this aspect, when the illumination light emitted from the light source is scanned by the scanning portion, the illumination light beams are radiated on to the individual scanning positions on the sample via the optical system, and the signal light beams emitted at the individual scanning positions are collected by the optical system. The detection signals are generated when the signal light beams are detected by the detector, and the generated detection signals are processed by the computer.

The light controller controls the irradiation positions and intensities of the illumination light beams at the sample in accordance with the periodic signals generated by the signal controller. In the computer, the frequencies of the detection signals generated by the detector are shifted by the frequency shifter by an amount corresponding to the period of the periodic signals generated by the signal controller, and, subsequently, the detection signals are integrated by the integrator at an integration time that is an integer multiple of the period of the periodic signals. By doing so, it is possible to separate and identify arbitrary signals from the detection signals detected in a mixed state.

In this case, with this embodiment, because a lock-in amplifier is not used to separate and identify signals, and the integrator that is operated in accordance with the periodic signals generated by the signal controller is used, a refresh rate required in the lock-in amplifier is not needed. Accordingly, it is possible to acquire an image of the sample by identifying the signals having the required sensitivity with a shorter exposure time and by assigning the identified signals to the individual scanning positions.

In the above-described aspect, the light controller may alternately switch the position or the intensity of the illumination light between two states thereof in accordance with the periodic signals.

In the above-described aspect, the signal controller may adjust, with reference to the periodic signals to be input to one of the light controller, the frequency shifter, and the integrator, phases of the periodic signals to be input to the other two components so that the other two components are operated together.

In the above-described aspect, the signal controller may be provided in one of the light controller, the frequency shifter, and the integrator.

The above-described aspect may be provided with an A/D converter that converts the detection signals to digital signals, wherein the frequency shifter may assign digital signs to the detection signals in accordance with the periodic signals, and the integrator may perform digital integration.

In the above-described aspect, the A/D converter may have an offset adjusting function.

By using an A/D converter having the offset function, it is possible to enhance the detection signal resolution.

In the above-described aspect, the illumination light beams may be radiated on to the sample via a plurality of pathways, and at least one of the light controller, the signal controller, and the computer may be provided in multiple units so as to correspond to the individual illumination light beams that travel via the individual pathways.

Another aspect of the present invention is an image-acquisition method including: a modulating step of temporally controlling, in accordance with periodic signals that are repeated at a predetermined period, a position or an intensity of illumination light emitted from a light source; a scanning step of scanning the illumination light controlled in the modulating step on a sample; a detecting step of detecting signal light beams generated at the individual scanning positions scanned in the scanning step and generating detection signals thereof; a frequency shifting step of shifting frequencies of the detection signals generated in the detecting step by an amount corresponding to the period of the periodic signals; and an integrating step of integrating the detection signals, which have been shifted in the frequency shifting step, at an integration time that is an integer multiple of the period of the periodic signals.

ADVANTAGEOUS EFFECTS OF INVENTION

The present invention affords an advantage in that it is possible to achieve a necessary sensitivity with a shorter exposure time as compared with a case in which a lock-in amplifier is used.

REFERENCE SIGNS LIST 1 image-acquisition apparatus
2, 24 light source
3, 20a, 20b light control portion (light controller)
4, 22 scanner (scanning portion)
5 objective lens (optical system)
8, 23 detector
9, 21a, 21b computing portion (computer)
11, 22a, 22b signal control portion (signal controller)
16 frequency shifter
17 integrator
19a, 19b laser light source (light source)
A sample
S1 modulating step
S2 scanning step
S3 detecting step
S4 frequency shifting step
S5 integrating step

The invention claimed is:

1. An image-acquisition apparatus comprising:
   a scanning portion that scans illumination light emitted from a light source;
   an optical system that focuses the illumination light scanned by the scanning portion on a sample, while collecting signal light beams generated at the individual scanning positions on the sample;
   a detector that detects the signal light beams collected by the optical system and that generates detection signals thereof;
   a controller that is configured to generate periodic signals that are repeated at a predetermined period;
   a light controller that is configured to temporally control a position or an intensity of the illumination light in accordance with the periodic signals generated by the signal controller; and
   a computer that is configured to process, in accordance with the periodic signals generated by the signal controller, the detection signals generated by the detector,
   wherein the computer is provided with a frequency shifter for shifting the frequency of the detection signals by an amount corresponding to the period of the periodic signals generated by the signal controller, and an integrator that integrates the detection signals, which have been shifted by the frequency shifter, at an integration time that is an integer multiple of the period of the periodic signals.

2. An image-acquisition apparatus according to claim 1, wherein the light controller alternately switches the position or the intensity of the illumination light between two states thereof in accordance with the periodic signals.

3. An image-acquisition apparatus according to claim 1, wherein the signal controller adjusts, with reference to the periodic signals to be input to one of the light controller, the frequency shifter, and the integrator, phases of the periodic signals to be input to the other two components so that the other two components are operated together.

4. An image-acquisition apparatus according to claim 3, wherein the signal controller is provided in one of the light controller, the frequency shifter, and the integrator.

5. An image-acquisition apparatus according to claim 1, further comprising:
   an A/D converter that converts the detection signals to digital signals,
   wherein the frequency shifter assigns digital signs to the detection signals in accordance with the periodic signals, and
   the integrator performs digital integration.

6. An image-acquisition apparatus according to claim 5, wherein the A/D converter has an offset adjusting function.

7. An image-acquisition apparatus according to claim 1, wherein the illumination light beams are radiated on to the sample via a plurality of pathways, and
   at least one of the light controller, the signal controller, and the computer is provided in multiple units so as to correspond to the individual illumination light beams that travel via the individual pathways.

8. An image-acquisition method comprising:
   a modulating step of temporally controlling, in accordance with periodic signals that are repeated at a predetermined period, a position or an intensity of illumination light emitted from a light source;
   a scanning step of scanning the illumination light controlled in the modulating step on a sample;
   a detecting step of detecting signal light beams generated at the individual scanning positions scanned in the scanning step and generating detection signals thereof;
   a frequency shifting step of shifting frequencies of the detection signals generated in the detecting step by an amount corresponding to the period of the periodic signals; and
   an integrating step of integrating the detection signals, which have been shifted in the frequency shifting step, at an integration time that is an integer multiple of the period of the periodic signals.

* * * * *